United States Patent
Suo

(10) Patent No.: US 11,801,241 B2
(45) Date of Patent: Oct. 31, 2023

(54) MUSCARINIC M2 RECEPTOR BLOCKADE TO DELAY OR PREVENT ONSET OF PROGRESSIVE MEMORY DECLINE

(71) Applicant: United States Government as Represented by The Department of Veterans Affairs, Washington, DC (US)

(72) Inventor: William Z. Suo, Kansas City, MO (US)

(73) Assignee: THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

(21) Appl. No.: 15/912,370

(22) Filed: Mar. 5, 2018

(65) Prior Publication Data

US 2018/0256559 A1  Sep. 13, 2018

Related U.S. Application Data

(60) Provisional application No. 62/467,024, filed on Mar. 3, 2017.

(51) Int. Cl.
| | | |
|---|---|---|
| *A61K 31/4545* | (2006.01) | |
| *A61K 9/00* | (2006.01) | |
| *A61P 25/28* | (2006.01) | |

(52) U.S. Cl.
CPC ........ *A61K 31/4545* (2013.01); *A61K 9/0053* (2013.01); *A61P 25/28* (2018.01)

(58) Field of Classification Search
CPC .... A61K 31/4545; A61K 9/0053; A61P 25/28
See application file for complete search history.

(56) References Cited

U.S. PATENT DOCUMENTS

| | | | |
|---|---|---|---|
| 7,252,953 B2 | 8/2007 | Suo et al. | |
| 2011/0020423 A1* | 1/2011 | Elenko | A61K 9/4858 424/432 |

FOREIGN PATENT DOCUMENTS

WO  WO2006008118  *  1/2006

OTHER PUBLICATIONS

Legg [online] (The Healthline Editorial Team (2016), pp. 1-9) Retrieved from the internet, Retrieved on Jan. 15, 2019, <url:https://www.healthline.com/health/alzheimers-disease/difference-dementia-alzheimers> (Year: 2016).*
PubChem CID9894173 [online] Retrieved from the internet, Retrieved on Jan. 15, 2019, <url: https://pubchem.ncbi.nlm.nih.gov/compound/9894173> (Year: 2006).*
Eglen et al. Pharmacology & Toxicology (1996), vol. 78, pp. 59-68 (Year: 1996).*
Puzzo et al. Biochem Pharmacol. 2014, vol. 88, pp. 450-467 (Year: 2014).*
Button et al. Nat Rev Neurosci. 2013, vol. 14, pp. 365-376 (Year: 2013).*
Reeves (Routes of Administraion and Dosage forms, Merck Manual, 2017, Reeves.pdf).*
Anderson, D., et al. "Can physical activity prevent physical and cognitive decline in postmenopausal women? A systematic review of the literature". Maturitas 79 (2014) 14-33.
Behrman, S. & Ebmeier, K.P. "Can exercise prevent cognitive decline?". Practitioner 258, 17-21, 2-3 (2014).
Boncristiano, S. et al. "Cholinergic changes in the APP23 transgenic mouse model of cerebral amyloidosis." The Journal of Neuroscience, 22, 3234-43 (2002).
Bonhomme, D. et al. "Vitamin A status regulates glucocorticoid availability in Wistar rats: consequences on cognitive functions and hippocampal neurogenesis?". Frontiers in Behavioral Neuroscience, vol. 8, Art 20 (2014).
Camps, P. et al, "Huprine X is a Novel High-Affinity Inhibitor of Acetylcholinesterase That Is of Interest for Treatment of Alzheimer's Disease". The American Society for Pharmacology and Experimental Therapeutics. Molecular Pharmacology, 57:409-417 (2000).
Clader, J.W., et al. "Muscarinic M2 antagonists: anthranilamide derivatives with exceptional selectivity and in vivo activity." Bioorganic & Medicinal Chemistry 12, 319-326 (2004).
De Strooper, B., Vassar, R. & Golde, T. "The secretases: enzymes with therapeutic potential in Alzheimer disease." Nat Rev Neural 6(2), 99-107 (2010).
Fisher, A. Cholinergic treatments with emphasis on m1 muscarinic agonists as potential disease-modifying agents for Alzheimer's disease.: Neurotherapeutics 5, 433-42 (2008).
Frick, K.M. & Benoit, J.D. "Use it or lose it: environmental enrichment as a means to promote successful cognitive aging." ScientificWorldJournal 10, 1129-41(2010).
Gainetdinov, R.R. et al. "Muscarinic supersensitivity and impaired receptor desensitization in G protein-coupled receptor kinase 5-deficient mice." Neuron vol. 24, 1029-36 (1999).
German, D.C., et al. "Cholinergic neuropathology in a mouse model of Alzheimer's disease." The journal of comparative neurology. 462:371-381 (2003).
Hardy, J. & Selkoe, D.J., "The amyloid hypothesis of Alzheimer's disease: progress and problems on the road to therapeutics." Science 297, 353-6 (2002).
Hernandez, D. et al. "Survival and plasticity of basal forebrain cholinergic systems in mice transgenic for presenilin-1 and amyloid precursor protein mutant genes." NeuroReport. vol. 12, 1377-84 (2001).
Hsiao, K. et al. "Correlative memory deficits, Abeta elevation, and amyloid plaques in transgenic mice." Science, New Series, vol. 274, No. 5284 (Oct. 4, 1996), pp. 99-102; Published by: American Association for the Advancement of Science.
Li, L., et al, "GRK5 deficiency exaggerates inflammatory changes in TgAPPaw mice." Journal of Neuroinflammation 5:24 (2008).

(Continued)

*Primary Examiner* — Kathrien A Hartsfield
(74) *Attorney, Agent, or Firm* — Ballard Spahr LLP

(57) ABSTRACT

Provided are methods for delaying or preventing onset of progressive memory decline by administering a muscarinic M2 receptor blocking compound to patients identified as at risk of developing a condition characterized by progressive memory decline, prior to onset of the condition.

11 Claims, 4 Drawing Sheets

(56) References Cited

OTHER PUBLICATIONS

Li, L. et al. "Augmented axonal defects and synaptic degenerative changes in female GRK5 deficient mice." Brain Research Bulletin 78, 145-51 (2009).
Liu, J. et al. "GRK5 deficiency leads to reduced hippocampal acetylcholine level via impaired presynaptic M2/M4 autoreceptor desensitization." Journal of Biological Chemistry vol. 284, No. 29 pp. 19564-19571 (2009).
Lambardo, J.A. et al. "Amyloid-B Antibody Treatment Leads to Rapid Normalization of Plaque-Induced Neuritic Alterations." Journal of Neuroscience 23(34):10879-10883 (2003).
Meinzer, M. et al. "Anodal transcranial direct current stimulation temporarily reverses age-associated cognitive decline and functional brain activity changes." Journal of Neuroscience 33(30), 12470-12478 (2013).
Morgan, D. "Immunotherapy for Alzheimer's disease." Journal of Alzheimer's Disease 9, 425-32 (2006).
Saenz, C., et al. "Estrogen contributes to structural recovery after a lesion." Neurosci Lett 392(3), 198-201 (2006).
Sandhir, R., et al. "A Coenzyme Q10 treatment ameliorates cognitive deficits by modulating mitochondrial functions in surgically induced menopause." Neurochemistry International 74, 16-23 (2014).
Sherwin, B. B. "Estrogen therapy: is time of initiation critical for neuroprotection?" Nat Rev Endocrinol 5, 620-7 (2009).
Singh, P., et al. "GRK5 deficiency leads to susceptibility to intermittent hypoxia-induced cognitive impairment." Behavioural Brain Research 302, 29-34 (2016).
Speisman, R. B. et al. "Environmental enrichment restores neurogenesis and rapid acquisition in aged rats." Neurobiol Aging 34, 263-7 4 (2013).
Spencer, J.P., "The impact of fruit flavonoids on memory and cognition." British Journal of Nutrition 104, S40-S47 (2010).
Sou, W.Z. & Lli, L., "Dysfunction of G protein-coupled receptor kinases in Alzheimer's disease." ScienceWorldJournal 10, 1667-78 (2010).
Sou, W. Z., "Accelerating Alzheimer's pathogenesis by GRK5 deficiency via cholinergic dysfunction." Advances in Alzheimer's Disease, vol. 2, No. 4, 148-160 (2013).
Tarumi, T. et al., "Cerebral hemodynamics of the aging brain: risk of Alzheimer disease and benefit of aerobic exercise." Frontiers in Physiology, vol. 5, Art. 6, (2014).
Vauzour, D. "Effect of flavonoids on learning, memory and neurocognitive performance: relevance and potential implications for Alzheimer's disease pathophysiology." Journal Sci Food Agric 94, 1042-56 (2014).
Wang, H., et al., "Repetitive transcranial magnetic stimulation applications normalized prefrontal dysfunctions and cognitive-related metabolic profiling in aged mice." PLoS One 8, e81482 (2013).
Bartus, R.T., et al., "The cholinergic hypothesis : a historical overview,current perspective, and future directions." Annals of the New York Academy of Sciences, vol. 444 , pp. 332-358 (1985).
Li, Y., Liu, Y ., Wang, z . & Jiang, Y . "Clinical trials of amyloid-based immunotherapy for Alzheimer's disease: end of beginning or beginning of end?" Expert Opinion on Biological Therapy,vol. 13, Issue 11, 1515-22 (2013).
Chen, J.F., "Adenosine receptor control of cognition in normal and disease." IInternational review of neurobiology, 119, 257-307 (2014).
Thathiah, A. & DE Strooper, B . "G Protein-coupled receptors, Cholinergic Dysfunction, and Aβ toxicity in Alzheimer' s disease." Science Signaling 2, re8 (2009).
Cheng et al. (2010) "GRK5 Deficiency Accelerates β-Amyloid Accumulation in Tg2576 Mice via Impaired Cholinergic Activity," *The Journal of Biological Sciences* 285(53): 41541-41548.
He et al. (2016) "GRK5 Deficiency Leads to Selective Basal Forebrain Cholinergic Neuronal Vulnerability," *Sci. Rep.* 6: 26116.
Suo et al. (2004) "Abnormality of G-Protein-Coupled Receptor Kinases at Prodromal and Early Stages of Alzheimer's Disease: An Association with Early β-Amyloid Accumulation," *The Journal of Neuroscience* 24(13): 3444-3452.
Suo et al. (2007) "GRK5 deficiency leads to early Alzheimer-like pathology and working memory impairment," *Neurobiology of Aging* 28(12): 1873-88.

\* cited by examiner

MUSCARINIC M2 RECEPTOR BLOCKADE TO DELAY OR PREVENT ONSET OF PROGRESSIVE MEMORY DECLINE

RELATED APPLICATION

The present application claims priority to U.S. provisional application No. 62/467,024, filed on 3 Mar. 2017, which is incorporated by reference in its entirety.

FIELD OF THE INVENTION

The present invention relates to the use of muscarinic M2 receptor blockade to delay or prevent onset of progressive memory decline.

BACKGROUND

Alzheimer's disease (AD) is a dementia clinically characterized by progressive memory loss and cognitive decline, and pathologically featured with selective cholinergic neurodegeneration. Millions of people in the United States, for example, are affected, yet there is no disease-modifying treatment. A disease-modifying therapy for AD should interfere with the disease process to slow down, stop or even reverse the disease progression. It should also include effective prevention therapy, meaning that if the treatment is given early enough before the disease onset, the treatment can significantly delay or prevent the actual onset.

Unfortunately, there is no effective preventative pharmaceutical approach to Alzheimer's disease available to date. Some treatments have claimed to be preventive, but the efficacies remain to be demonstrated or have been proven wrong. For instance, cholinesterase inhibitors (ChEIs) were once claimed to prevent AD, but it is now clear that ChEIs have no preventive effect. Blocking of presynaptic muscarinic M2 receptor is known to increase acetylcholine release, which was believed to be able to compensate the cholinergic hypofunctioning in AD. There was a pharmaceutical campaign in the 1990's to make use of M2 antagonists as alternative cholinomimetic drugs to the cholinesterase inhibitors. However, that effort eventually failed because, even though the entire category of cholinomimetic drugs were essentially effective only as symptom management drugs, the M2 blockers were even less potent as compared to ChEIs.

Similarly, the efficacy of estrogen on cognitive decline is in question because it does not work in most cases, except for when administered around the time of menopause. Aβ vaccination had great results in animal models, but failed on human trials due to severe side effects. The use of monoclonal antibody against Aβ was once hopeful but the most recent failure of the phase 3 trial for Solanezumab was just announced by Eli Lily. See Honig L S, Vellas B et al., *Trial of Solanezumab for Mild Dementia Due to Alzheimer's Disease. N Engl J Med.* 2018 Jan. 25; 378(4):321-330. Trials on caffeine-based reduction of on adenosine receptors on cognitive decline on in are still ongoing.

Some non-pharmaceutical approaches may be partially effective for AD prevention. For example, some common approaches known to delay aging or aging-related diseases are believed to delay AD onset as well. These may include physical exercise, dietary supplements, environmental enrichment, and physical therapy.

Therefore, even though numerous treatment and prevention efforts are known in the art, there is still a need for a preventative pharmaceutical approach to diseases that are at least in part characterized by progressive memory decline. The present invention provides such an approach.

SUMMARY

Provided herein is a method for delaying or preventing onset of progressive memory decline in patients in need of such treatment, wherein said method comprises identifying a patient that is at risk of developing a condition characterized by progressive memory decline; and administering to the patient, prior to onset of the condition, a therapeutically effective amount of a muscarinic M2 receptor blocking compound; wherein the patient has not been diagnosed as currently experiencing a condition characterized by progressive memory decline at the time of administration of the muscarinic M2 receptor blocking compound, is provided.

As used herein, the terms "treat", "treating," and "treatment" refer to at least one of (a) preventing the onset of a disease or disorder altogether and (b) delaying the onset of the disease or disorder or at least one of the clinical symptoms of a disease or disorder in a subject which may be predisposed to a disease or disorder even though that subject does not yet experience or display symptoms of the disease or disorder.

Also provided is a method where the patient is identified as being at risk of developing dementia. Also provided is a method where the patient is identified as being at risk of developing Alzheimer's disease. Also provided is a method where the patient is identified as being at risk of developing early onset Alzheimer's disease. In one embodiment, a muscarinic M2 receptor blocking compound is initially administered prior to patient's onset of memory decline. Also provided is a method where the muscarinic M2 receptor blocking compound is administered orally.

In another aspect of the inventive subject matter, provided is a method comprising identifying a subject that is at risk of developing a condition characterized by progressive memory decline; administering a therapeutically effective amount of a muscarinic M2 receptor blocking compound to the subject prior to onset of progressive memory decline; and delaying onset of progressive memory decline in the subject by repeated administration of the therapeutically effective amount of a muscarinic M2 receptor blocking compound to the subject. Also provided is a method where the subject has not been diagnosed as currently experiencing the condition characterized by progressive memory decline at a time of a first administration of the muscarinic M2 receptor blocking compound. Also provided is a method where the condition characterized by progressive memory decline is dementia. Also provided is a method where the condition characterized by progressive memory decline is Alzheimer's disease. Also provided is a method where the subject is identified as being at risk of developing early onset Alzheimer's disease. Also provided is a method where the first administration of the muscarinic M2 receptor blocking compound is prior to the subject's onset of memory decline. Also provided is a method where the muscarinic M2 receptor blocking compound is administered orally.

In yet another aspect of the inventive subject matter, provided is a method comprising identifying a subject that is at risk of developing a condition characterized by progressive memory decline; and delaying onset of progressive memory decline in the subject by repeated administration of a therapeutically effective amount of a muscarinic M2 receptor blocking compound to the subject. Also provided is a method where the subject has not been diagnosed as currently experiencing the condition characterized by progressive memory decline at a time of a first administration of the muscarinic M2 receptor blocking compound. Also provided is a method where the condition characterized by progressive memory decline is dementia. Also provided is a method where the condition characterized by progressive memory decline is Alzheimer's disease. Also provided is a method where the subject is identified as being at risk of developing early onset Alzheimer's disease. Also provided is a method where the first administration of the muscarinic M2 receptor blocking compound is prior to the subject's onset of memory decline. Also provided is a method where the muscarinic M2 receptor blocking compound is administered orally.

Other features and advantages of the present invention will become more readily apparent to those of ordinary skill in the art after reviewing the following detailed description and accompanying drawings.

BRIEF DESCRIPTION OF THE DRAWINGS

The methods of the present invention will be understood from a review of the following detailed description and the accompanying drawings:

FIG. 5A shows preventive effect of AAD23 in terms of entries into goal quadrant. FIG. 5B shows preventive effect of AAD23 in terms of time (sec) in goal quadrant. FIG. 5C shows preventive effect of AAD23 in terms of distance (m) in goal quadrant. FIG. 5D shows preventive effect of AAD23 in terms of latency (sec) to goal quadrant. These are additional results in support of the MWM platform experiment described in data presented in FIG. 4. The results showed significant effects (as indicated) of AAD23 on spatial reference memory if use the parameters of goal quadrant as the measurements.

DETAILED DESCRIPTION

Figure 1:
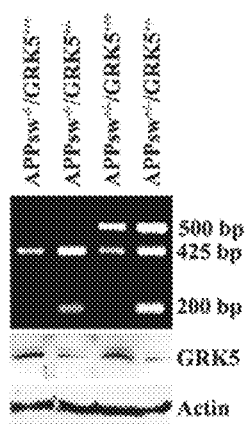
FIG. 1 shows genotypes and GRK5 expression in TgAPPsw mice with reduced GRK5 (GAP) mice. Top panel, an example of the genotyping results for the WT (APPsw$^{-/-}$/GRK5$^{+/+}$), GRK5-Heterozygote (APPsw$^{-/-}$/GRK5$^{+/-}$), TgAPPsw (APPsw$^{+/-}$/GRK5$^{+/+}$) and the GAP mice (APPsw$^{+/-}$/GRK5$^{+/-}$) using the ascribed five primers. 500 base pair (bp) band, human APPsw; 425 bp band, WT GRK5; 200 bp band, inactivated GRK5. Bottom panels are representative Western blots for GRK5 and β-actin (internal control for the amount of sample loaded).

Unless otherwise defined herein, scientific, clinical, and technical terms used in connection with the present invention shall have the meanings that are commonly understood by those of ordinary skill in the art. Further, unless otherwise required by context, singular terms shall include pluralities and plural terms shall include the singular.

All patents and other publications identified are expressly incorporated herein by reference in their entirety for the purpose of describing and disclosing, for example, the methodologies described in such publications that might be used in connection with information described herein.

Certain embodiments disclosed herein provide for a method for delaying or preventing onset of progressive memory decline in patients in need of such treatment, wherein said method comprises identifying a patient that is at risk of developing a condition characterized by progressive memory decline; and administering to the patient, prior to onset of the condition, a therapeutically effective amount of a muscarinic M2 receptor blocking compound; wherein the patient has not been diagnosed as currently experiencing a condition characterized by progressive memory decline at the time of administration of the muscarinic M2 receptor blocking compound, is provided. Also provided is a method where the patient is identified as being at risk of developing dementia. Also provided is a method where the patient is identified as being at risk of developing Alzheimer's disease. Also provided is a method where the patient is identified as being at risk of developing early onset Alzheimer's disease. In one embodiment, a muscarinic M2 receptor blocking compound is initially administered prior to patient's memory decline. Also provided is a method where the muscarinic M2 receptor blocking compound is administered orally.

Also provided is a method comprising identifying a subject that is at risk of developing a condition characterized by progressive memory decline; administering a therapeutically effective amount of a muscarinic M2 receptor blocking compound to the subject prior to onset of progressive memory decline; and delaying onset of progressive memory decline in the subject by repeated administration of the therapeutically effective amount of a muscarinic M2 receptor blocking compound to the subject. Also provided is a method where the subject has not been diagnosed as currently experiencing the condition characterized by progressive memory decline at a time of a first administration of the muscarinic M2 receptor blocking compound. Also provided is a method where the condition characterized by progressive memory decline is dementia. Also provided is a method where the condition characterized by progressive memory decline is Alzheimer's disease. Also provided is a method where the subject is identified as being at risk of developing early onset Alzheimer's disease. Also provided is a method where the first administration of the muscarinic M2 receptor blocking compound is prior to the subject's onset of memory decline. Also provided is a method where the muscarinic M2 receptor blocking compound is administered orally.

Also provided is a method comprising identifying a subject that is at risk of developing a condition characterized by progressive memory decline; and delaying onset of progressive memory decline in the subject by repeated administration of a therapeutically effective amount of a muscarinic M2 receptor blocking compound to the subject. Also provided is a method where the subject has not been diagnosed as currently experiencing the condition characterized by progressive memory decline at a time of a first administration of the muscarinic M2 receptor blocking compound. Also provided is a method where the condition characterized by progressive memory decline is dementia. Also provided is a method where the condition characterized by progressive memory decline is Alzheimer's disease. Also provided is a method where the subject is identified as being at risk of developing early onset Alzheimer's disease. Also provided is a method where the first administration of the muscarinic M2 receptor blocking compound is prior to the subject's onset of memory decline. Also provided is a method where the muscarinic M2 receptor blocking compound is administered orally.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

Unlike previous applications of muscarinic M2 receptor blockers in Alzheimer's disease it was discovered that blockade of muscarinic presynaptic M2 receptor by application of an M2 receptor blocker, prior to disease onset, produced a preventative effect, delaying, or preventing onset of progressive memory decline. Behavioral tests performed after the acute drug effects were completely washed off and no longer in effect to ensure the treatment was disease-modifying, confirmed this result. This invention makes use of muscarinic M2 receptor blocking compounds and the strategy to block M2 receptors for correcting cholinergic neuronal vulnerability that is independent of the acetylcholine release. As described herein, the efficacy of this strategy was demonstrated and was superior and specific for preventing spatial memory decline.

Certain types of progressive memory impairments can cause permanent damage to the brain, which cannot be reversed. For example, memory loss is one of the first or more-recognizable signs of dementia. Dementia is not a specific disease but a set of symptoms, including impairment in memory, reasoning, judgment, language, and other thinking skills. Dementia can be caused by Alzheimer's disease, cerebrovascular conditions (e.g., multi-infarct disease and stroke), frontotemporal conditions, Lewy body disease, Parkinson's disease, Huntington's disease, and other diseases and conditions.

Alzheimer's disease is a dementia clinically characterized by progressive memory loss and cognitive decline and is the most common form of dementia. Alzheimer's disease most commonly affects older adults, 65 or over ("late onset"), but when it is diagnosed in younger patients, it is referred to "early-onset" or "younger-onset" Alzheimer's disease.

Early-onset Alzheimer's disease can develop at any time in a person's life from their 20's to early 60's, typically affecting people in their 50's. Familial Alzheimer's is a form of early-onset where a genetic predisposition leads to the disease. People with a parent, or sibling with Alzheimer's are more likely to develop the disease themselves, with the risk increasing if more than one family member has the disease. When the disease runs in families, genetic or environmental factors, or both, may play a role. Certain inherited gene mutations have been identified as causing this form of the disease. FAD mutations, for example, include mutations on chromosome 21 causing the formation of abnormal amyloid precursor protein (APP), mutations on chromosome 14 causing formation of abnormal presenilin-1 (PS-1), and mutations on chromosome 1 causing formation of abnormal presenilin-2 (PS-2).

The known FAD gene mutation carriers are usually identified based on family history and pedigree analysis, and confirmed by sequencing their three FAD genes (APP, PS1 and PS2) for mutations. Once a known mutation is found, no further test is needed.

Down syndrome patients are usually identified early in their life by chromosome examination.

The APOE ε4 allele of the apolipoprotein E (APOE) gene on chromosome 19 has been identified as a risk-factor gene for Alzheimer's disease because it increases the risk of developing the disease and is also associated with an earlier age of disease onset. However, inheriting an APOE ε4 allele does not definitely mean the person will develop Alzheimer's disease. Typically, a person has up to two alleles, having more alleles increases the risk of developing the disease. The APOE ε2 allele may provide some protection against the disease, if Alzheimer's disease occurs, it usually develops later in life than it would in someone having the APOE ε4 allele.

For people with a high risk of developing Alzheimer's disease, it is necessary to consider a combination of multiple factors. The factors include but not limited to the following:

(1) Memory complaint with the Mini Mental State Examination (MMSE) or other memory test indicating mild cognitive impairment (MCI);
(2) ApoE allele assay revealing as ε4 allele carrier;
(3) Age is older than 65;
(4) Female;
(5) Having a family member or relatives suffering from AD (even though no known mutations are identified);
(6) Medical history of having other related disease such as cardiovascular diseases, stroke, diabetes, brain trauma, etc
(7) Functional MRI (fMRI) revealing reduced cerebral blood flow and brain metabolism.
(8) Others, such as GRK5 deficiency.

These factors altogether may point a particular patient having high risk (the more factors, the higher risks) of developing AD later on. These patients would be considered a high priority population in need of preventive therapy.

Reference to family history of onset and progression of disease in affected family members can be used to inform treatment strategies, such as timing of initial administration of a muscarinic M2 receptor blocking compound, as well as dose frequency and duration.

Muscarinic M2 receptor blocking compounds. Muscarinic M2 receptor antagonists are well known in the art. Such compounds include, but are not limited to, the anthranilamide derivative known as AAD23 and methoctramine (MT) that are used in the art. Other examples of M2 receptor antagonists including earlier dibenzodiazepinone-based compounds (such as BIBN 99, YM-59981, and DIBD), tripitramine, 3-α-Chloroimperialine, Himbacine, piperidine, and recently described allosteric modulators of M2 receptors, etc.

Memory decline may be evaluated by any number of methods known in the art, including, for example, taking a medical history and performing physical and/or neurological examinations. Memory complaint with the Mini Mental State Examination (MMSE) or other memory test indicating mild cognitive impairment (MCI) tests may be used. Imaging of the brain using functional magnetic resonance imaging (fMRI) may also be used.

As discussed above, the term "treatment" as used herein refers to at least one of (a) preventing the onset of a disease or disorder altogether and (b) delaying the onset of the disease or disorder or at least one of the clinical symptoms of a disease or disorder in a subject which may be predisposed to a disease or disorder even though that subject does not yet experience or display symptoms of the disease or disorder.

As used herein, "therapeutically effective amount" refers to the amount of a compound that, when administered to a subject for delaying or preventing onset of progressive memory decline, is sufficient to affect such treatment. The "therapeutically effective amount" can vary depending on the compound, the disease or disorder, the age of the subject to be treated, and/or the weight of the subject to be treated, for example. Accordingly, this term is not limited to a single dose, but may comprise multiple dosages required to bring about a therapeutic or prophylactic response in the subject. An appropriate amount in any given instance can be readily apparent to those skilled in the art or capable of determination by routine experimentation.

Pharmaceutical compositions that comprise a therapeutically effective amount of muscarinic M2 receptor blocking compound are administered to a patient in a manner appropriate to the indication. The muscarinic M2 receptor blocking compound may be administered via oral, mucosal (including sublingual, buccal, rectal, nasal, or vaginal), parenteral (including subcutaneous, intramuscular, bolus injection, intra-arterial, or intravenous), transdermal, or topical administration. The muscarinic M2 receptor blocking compound may be in a form suitable for oral use, for example, as tablets, troches, lozenges, aqueous or oily suspensions, dispersible powders or granules, emulsions, hard or soft capsules, or syrups or elixirs.

The following examples, including the experiments conducted and the results achieved, are provided for illustrative purposes only and are not to be construed as limiting the scope of the appended claims.

EXAMPLES

Example 1

Animal preparation. The creation of GAP mice was achieved by cross-breeding GRK5KO mice with Tg2576 (TgAPPsw) mice. GRK5KO mice were previously generated by targeted deletion of exons 7 and 8 of the GRK5 gene, encoding critical sub-elements I through III of the protein kinase catalytic domain, as detailed previously. Tg2576 mice were developed by Hsiao et al previously by overexpression of human APP gene carrying the Swedish mutations. See Hsiao, K. et al. Correlative memory deficits, Abeta elevation, and amyloid plaques in transgenic mice. Science 274, 99-102. (1996). Both strains have been previously bred with C57/BL6 mice for more than 10 generations, therefore all having the same genetic background. After breeding these two strains of mice, the resulted offspring were genotyped to identify those that contain both genetic modifications (FIG. 1). The genotyping protocol is described in detail as the following.

Mouse-tail DNA was prepared and genotyping was performed as previously described. See Li, L., Liu, J. & Suo, W. Z. GRK5 deficiency exaggerates inflammatory changes in TgAPPaw mice. J Neuroinflammation 5, 24 (2008). Genotyping was performed by polymerase chain reaction (PCR) amplification of the tail genomic DNA using two human APP-specific primers which amplify a 500 bp DNA fragment and were used to identify the presence of the human APP transgene; three additional primers specific for wild type (WT) murine GRK5 (425 bp) and the GRK5KO loci (200 bp) which were used to identify the presence of WT or the targeted murine GRK5 gene. PCR was used for amplification. The 20 µl reaction volume contained 1.25 units of Flexi DNA polymerase (Promega, Madison, Wis.), 200 µM dNTPs, 2 mM MgCl2, and 250 nM of each of the APP primers and 1 µM of each of the three GRK5 primers. The amplification protocol entailed 35 cycles of denaturation at 94° C. for 15 s, annealing at 62° C. for 15 s and extension at 72° C. for 15 s, and then followed by a 10-min final extension at 72° C. The PCR products (10 µl) were then analyzed and visualized on 2.0% agarose gels. FIG. 1 shows an example of typical genotyping result including the four different genotypes used in this application.

Since these mice have been shown to display gender differences, only female GAP mice were used for the experiments. See e.g., Li, L., Liu, J. & Suo, W. Z. GRK5 deficiency exaggerates inflammatory changes in TgAPPaw mice. J Neuroinflammation 5, 24 (2008); Li, L. et al. Augmented axonal defects and synaptic degenerative changes in female GRK5 deficient mice. Brain Res Bull 78, 145-51 (2009); and Suo, W. Z. & Li, L. Dysfunction of G protein-coupled receptor kinases in Alzheimer's disease. Science World Journal 10, 1667-78 (2010). There were a total of 30 female GAP mice for this experiment at the beginning. They were randomly grouped into two arms for AAD23 treatment (n=8) and control (n=22).

T h e GAP mouse is the Swedish APP mice (Tg2576 or APPsw) deficient in G-protein coupled receptor kinase-5 (GRK5). Compared to APPsw mice, GAP mice displayed more severe pathological changes such as more Aß, plaques, and inflammation, as well as more prominent cholinergic neurodegeneration that other AD models lack. See e.g., Hernandez, D. et al. Survival and plasticity of basal forebrain cholinergic systems in mice transgenic for presenilin-1 and amyloid precursor protein mutant genes. Neuroreport 12, 1377-84 (2001); Boncristiano, S. et al. Cholinergic changes in the APP23 transgenic mouse model of cerebral amyloidosis. J Neurosci 22, 3234-43 (2002); and German, D. C. et al. Cholinergic neuropathology in a mouse model of Alzheimer's disease. J Comp Neurol 462, 371-81 (2003).

Example 2

Figure 2:
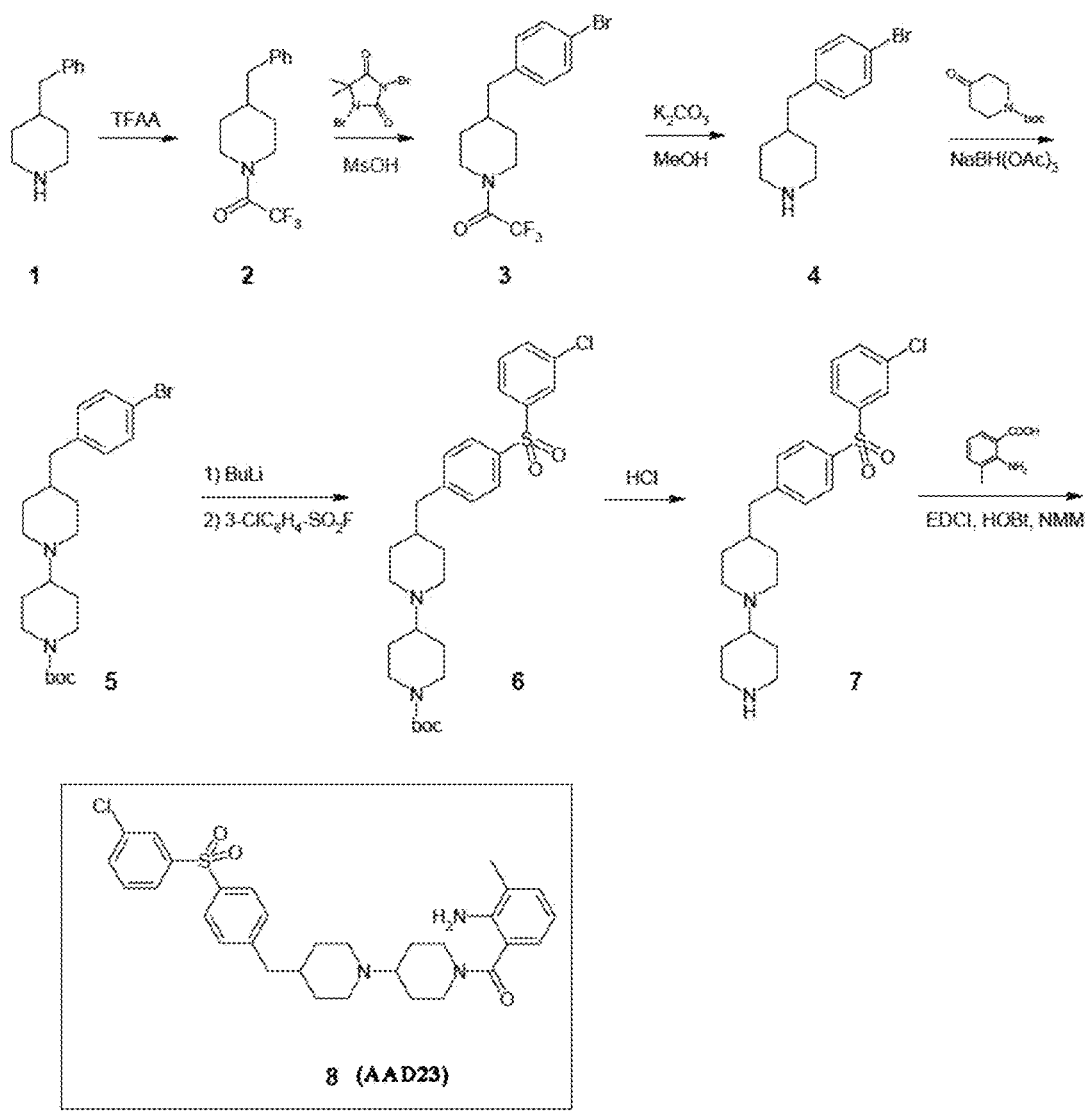
FIG. 2 shows a scheme of AAD23 synthesis.

Drug Synthesis. Synthesis and purification of an anthranilamide derivative, AAD23, was completed step-by-step as shown below and in FIG. 2. A synthetic method is also provided in Clader, J. W. et al. Muscarinic M2 antagonists: anthranilamide derivatives with exceptional selectivity and in vivo activity. Bioorganic & Medicinal Chemistry 12, 319-326 (2004).

Compound 3: A solution of 4-benzylpiperidine 3 (Compound 1) (202 g, 1.15 mol) in dichloromethane (1.5 L) was treated with 216 ml (1.53 mol) of trifluoroacetic anhydride (TFAA) added drop-wise over 30 min to produce trifluoroacetic 4-benzylpiperidine (Compound 2). The mixture was allowed to stir an additional 90 minutes at room temperature and then cooled to 0° C. in an ice bath. Methanesulfonic acid (MsOH) (306 ml) was added in portions followed by dibromodimethylhydantoin (171 g, 0.6 mol) also added in portions, and the resulting mixture was stirred overnight while coming to room temperature. After again cooling in an ice bath, the mixture was quenched by addition of saturated Na$_2$S0$_3$ (1.6 L) added over 30 minutes. The aqueous layer was separated and washed with dichloromethane (2×2 L). The combined organic layers were dried over magnesium sulfate and concentrated. The residue was purified by silica gel chromatography, eluting with hexanes, 5% ethyl acetate-hexane, and 10% ethyl acetate-hexane to yield 52 g of compound 3, which was used directly in the next step.

Compound 4: A solution of compound 3 in 890 ml methanol was treated with 47 g potassium carbonate in 157 ml water. The mixture was stirred for 3 hours, then concentrated under vacuum. The residue was treated with 2 N NaOH (1 L) and extracted with dichloromethane (2×1 L). The combined organic layers were dried over magnesium sulfate and evaporated to give 38.4 g of compound 4 as oil.

Compound 5: A suspension of compound 4 in 500 ml dichloromethane was treated with 1-tert-butoxycarbonyl-4-piperidone (32.3 g), glacial acetic acid (19.2 ml), and sodium triacetoxyborohydride (97 g). The mixture was allowed to stir overnight at room temperature, then poured into 2 N NaOH (1 L). After stirring an additional 30 minutes, the layers were separated, and the aqueous layer was extracted with ethyl acetate (2×700 ml). The combined organic layers were dried over magnesium sulfate and evaporated, and the residue was purified by flash chromatography, eluting with ethyl acetate to give 28.9 g of compound 5.

Compound 6: A solution of compound 5 (28 g) in 115 ml dry THF at −78° C. was treated with 26.4 ml of 2.5 M n-butyllithium in hexanes followed by a solution of 3-chlorobenzenesulfonyl fluoride (13 g, prepared from 3-chlorobenzenesulfonyl chloride and KF) in 70 ml of dry THF. The mixture was stirred at −78° C. for 2 hours then allowed to come to room temperature overnight. The reaction was quenched with water, concentrated under vacuum, and partitioned between ethyl acetate and 10% sodium carbonate. The organic layer was washed with water, dried over magnesium sulfate, and evaporated. The residue was purified over silica gel, eluting with 5% methanol-ethyl acetate, and the purified residue was crystallized from ethyl acetate to give 7.9 g of compound 6.

Compound 7: To a cooled (0° C.) mixture of 6 (7.9 g), CH2Cl2 (60 ml) and H2O (0.35 ml) trifluoroacetic acid (15 ml) was added dropwise. The cooling bath was removed and the mixture was stirred for 2 hours. The volatile materials were removed in vacuo, CH$_2$Cl$_2$ (60 ml) and 10% NaOH (50 ml) was added, and the resulting mixture was stirred for 3 minutes. The CH$_2$Cl$_2$ layer was removed, the aqueous layer was extracted with CH$_2$Cl$_2$ (3×50 ml), the organic extracts were dried over Na$_2$SO$_4$, filtered and evaporated to give compound 7 as a white foam (6.5 g).

Compound 8: EDC (4.3 g) was added to a mixture of the compound 7 (6.5 g), dimethylformamide (215 ml), hydroxobenzotriazole (3 g), diisopropylethylamine (11 ml), and the benzoic acid (3.4 g). The resulting solution was stirred at room temperature overnight and then partitioned between 1000 ml of ethyl acetate and 110 ml 2 N sodium hydroxide. The aqueous layer was extracted with ethyl acetate (3×300 ml), and the combined organic layers were dried over sodium sulfate and evaporated. The residue was purified by silica gel flash chromatography to give the crude compound 8 as its free base. The free base was dissolved in 200 ml ethyl acetate and treated with 15 ml of 2 M HCl in Et2O at 0° C. The salt was precipitated by addition of ether, filtered, washed with ether, and dried under vacuum to give the HCl salt. The above salt was recrystallized from i-PrOH and treated with 2N NaOH—CH2Cl2. Organic phase was dried with sodium sulfate and evaporated to give 5.1 g of 98% pure compound 8 (AA023), according to LC-MS data.

Example 3

Drug administration. AAD23 dosing was pre-determined in an acute experimental model in the GAP mice, and the optimal dose was between 2-3 mg/kg, if given orally. For actual animal treatment, it was administered orally by incorporating it into the diet with a concentration of 18.75 mg/kg dry diet M8626D (prepared by Harlan Laboratories). If in average an adult mouse weights 30 grams, and consumes approximately 4 grams of diet, it equals to take 2.5 mg/kg of the drug daily. In order to distinguish the drug-containing diet, non-toxic food color (pink) was added. This compound has no bad smell or taste that significantly affected the amount of diet consumed, according to our observation. For a 6-month drug treatment plan, incorporation of the drug into the diet was the way with the least stress for the animals.

Example 4

Behavioral tests. Both AAD23-treated and untreated control mice were transferred to behavioral testing room immediately after preventing the drug treatment. They were housed in the behavioral room for two weeks to adapt to the new environment before being subjected to open field, balance beam, string agility, elevated plus maze, swimming prescreening, Y maze and Morris water maze tests.

The two-week behavioral test battery provided an essential analysis of sensorimotor functioning, anxiogenic tendencies, and mnemonic performance. For all behavioral testing, the operator was blind to the experimental variables of genotypes and treatments (all animals were randomly coded throughout the experiments). Standard stress control and habituation procedures applied. All tests were monitored and recorded by Stoelting Any Maze™ Video Tracking System. The detailed behavioral test protocol may found in our previous publications. See Singh, P. et al GRK5 deficiency leads to susceptibility to intermittent hypoxia-induced cognitive impairment. Behav Brain Res 302, 29-34 (2016). Below is a brief description of the methods.

Open Field evaluated activity/exploratory behavior (1 day). The total travel distance in the open field over a 3-minute period was analyzed.

Balance Beam evaluated vestibular and general motor balance (1 day). Latency to fall from a beam in 3 successive trials (60 seconds maximum) was analyzed.

String Agility evaluated agility and grip capacity (1 day). Animals were permitted to grasp a suspended string only by their forepaws and then released. During a single 60 second trial, each animal was assessed using a 0-5 rating system.

Elevated Plus-Maze evaluated level of anxiety (1 day). Closed and open arm entries over a 3-minute period were analyzed.

Swimming Screening excluded potential swimming deficiency or dismotivation (1 day). 15-sec rest on platform followed by 75-sec free-swimming/exploration. Free-floating or idling mice (none for these groups) were removed from subsequent cognitive tests.

Y-Maze evaluated spontaneous alternation behavior and mnemonic spatial memory (1 day). Correct (different from previous two entries) arm entry rate was analyzed.

Morris Water Maze (MWM) evaluated spatial reference learning over 5 days and spatial reference memory in three intermediate and one final probe trial on day 6. The Morris water maze trained the animals to remember a platform in goal quadrant for escaping from the water no matter where they start, therefore it tested the animal's spatial reference memory. For the probing trial, the platform was removed. The animals that remembered where the platform used to be entered that area quicker (shorter latency).

Data Collection, Analysis and Report.

Figure 3:
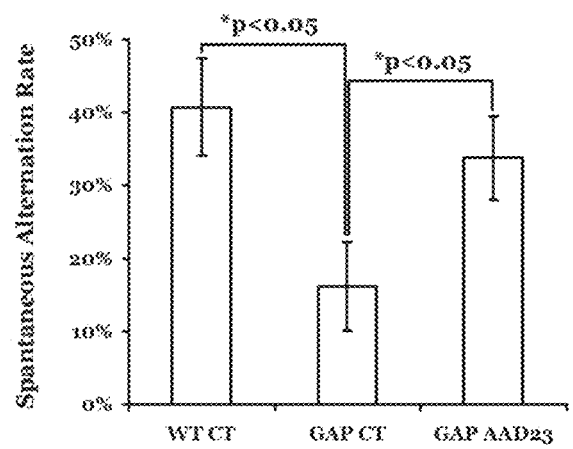
FIG. 3 shows preventive effect of AAD23 on spontaneous alternation rate of GAP mice in Y maze. Spontaneous alternation in Y maze tests animal's short term spatial memory due to rodents' innate tendency to explore a novel environment. The animal's performance was rated correct only when they chose an arm that was different from previous two entries. The WT control had a correct rate of 40%, whereas the GAP mice at 12 months displayed a significantly (p<0.05) reduced correct rate below 20%. By contrast, the AAD23 treated GAP mice showed a correct rate of 34%, which was significantly (p<0.05) better than the untreated GAP mice.
Figure 4:
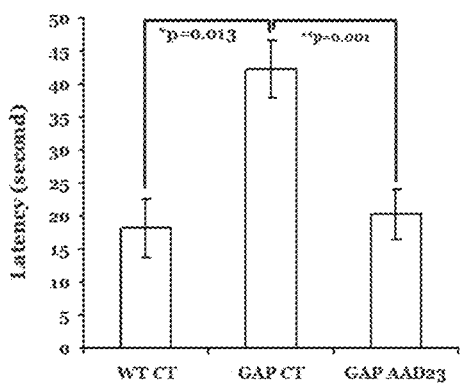
FIG. 4 shows preventive effect of AAD23 on Morris Water Maze (MWM) platform probing test of GAP mice. The WT mice at 12-months of age had an average latency of 18.2 seconds to first enter the platform area, while the untreated GAP mice at the same age spent significantly longer time (42.2 Sec, p=0.013) to enter the platform area. In contrast, the AAD23 treated GAP mice at 12-months of age spent much less time (22.3 sec, p=0.001) to first enter the platform area, than the untreated GAP mice.
Figure 5A:
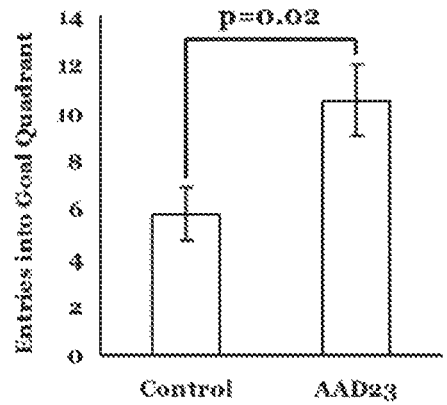
FIGS. 5A, 5B, 5C, and 5D show preventive effect of AAD23 on MWM platform probing test of GAP mice.
Figure 5B:
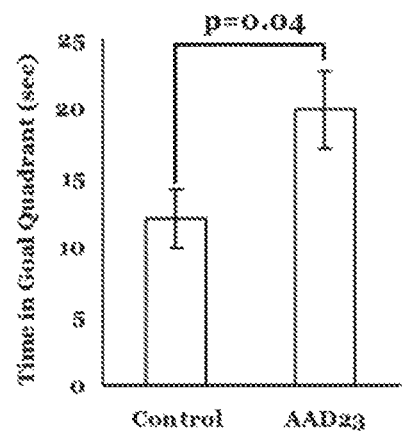
Figure 5C:
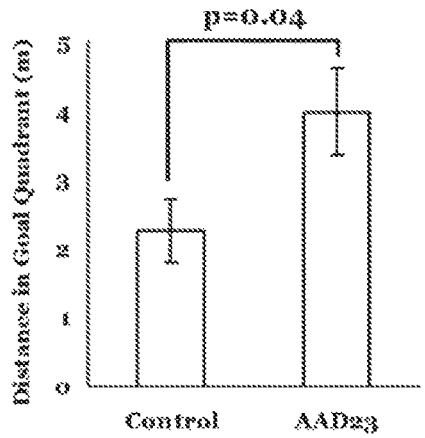
Figure 5D:
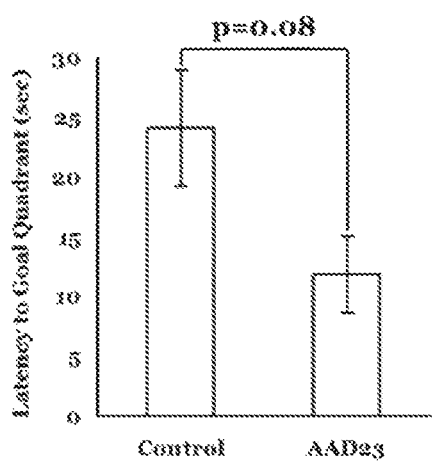

For the behavioral test results, no significant differences were identified between any groups for open field, balance beam, string agility and elevated plus maze tests, indicating these animals were not impaired for their sensorimotor function and anxiogenic tendencies. However, for the two tasks that measure mnemonic performance (Y maze and MWM), the untreated GAP mice were known to be impaired at 12-month for Y maze spontaneous alternation and MWM platform probing, according to our previous data. With 6 months of treatment of AAD23, they performed significantly better than those untreated GAP mice, and their levels of performance were as good as the WT mice (FIGS. 3, 4, and 5). These results suggest that 6 months of AAD23 treatment significantly prevented the memory decline in the GAP mice.

Thus, a pharmaceutical approach has been disclosed, specifically blocking presynaptic muscarinic M2 receptor, and successfully preventing memory decline in GAP mice. It should be apparent, however, to those skilled in the art that approaches besides those already described are possible without departing from the inventive concepts herein. The inventive subject matter, therefore, is not to be restricted except in the spirit of the disclosure. Moreover, in interpreting the disclosure all terms should be interpreted in the broadest possible manner consistent with the context. In particular the terms "comprises" and "comprising" should be interpreted as referring to the elements, components, or steps in a non-exclusive manner, indicating that the referenced elements, components, or steps can be present, or utilized, or combined with other elements, components, or steps that are not expressly referenced.

What is claimed is:

1. A method for delaying onset of progressive memory decline, the method comprising administering to a patient having a GRK5 deficiency a therapeutically effective amount of AAD23, wherein the GRK5 deficiency is identified prior to onset of a condition characterized by progressive memory decline, wherein the administering step is prior to onset of the condition, and wherein the patient has not been diagnosed as currently experiencing Alzheimer's disease, Parkinson's disease, Huntington's disease, or dementia at the time of administration of AAD23.

2. The method of claim 1, wherein administering is repeated administration, and wherein the patient has not been diagnosed as currently experiencing a cognitive disorder at the time of first administration of AAD23.

3. The method of claim 1, wherein AAD23 is administered orally.

4. The method of claim 1, wherein the patient has not been diagnosed as currently experiencing a cognitive disorder at the time of administration of AAD23.

5. The method of claim 1, wherein the patient is age 65 or over.

6. The method of claim 1, wherein the patient is age 20 to 60.

7. The method of claim 1, wherein the method comprises administering a pharmaceutical composition comprising AAD23.

8. The method of claim 7, wherein the composition is formulated as a tablet, troche, lozenge, or capsule.

9. The method of claim 7, wherein the composition is formulated as an aqueous or oil suspension, a dispersible powder or granule, an emulsion, a syrup, or an elixir.

10. The method of claim 1, wherein the therapeutically effective amount is a dosage of 2 mg/kg to 3 mg/kg.

11. The method of claim 1, wherein the therapeutically effective amount is a dosage of about 2.5 mg/kg.

* * * * *